United States Patent [19]

McFarlane

[11] Patent Number: 4,921,096
[45] Date of Patent: May 1, 1990

[54] PACKAGE ASSEMBLY

[75] Inventor: Richard McFarlane, Geneva, Ill.

[73] Assignee: Taut, Inc., Geneva, Ill.

[21] Appl. No.: 297,126

[22] Filed: Jan. 17, 1989

[51] Int. Cl.$^5$ .............................................. B65D 85/20
[52] U.S. Cl. ..................................... 206/349; 206/363; 206/365
[58] Field of Search ............... 206/363, 364, 365, 367, 206/368, 349, 361; 220/339

[56] References Cited

U.S. PATENT DOCUMENTS

| | | | |
|---|---|---|---|
| 2,570,412 | 10/1951 | Vogel | 206/361 |
| 3,008,570 | 11/1961 | Roehr et al. | 206/364 |
| 3,154,192 | 10/1964 | Cowley | 206/379 |
| 3,342,319 | 9/1967 | Faulseit | 206/365 |
| 3,904,035 | 9/1975 | Metzler et al. | 206/379 |
| 4,294,558 | 10/1981 | Errichiello | 220/339 |
| 4,356,919 | 11/1982 | Matney | 206/493 |
| 4,417,613 | 11/1983 | Ryan et al. | 220/339 |
| 4,546,881 | 10/1985 | Tasma | 206/459 |
| 4,659,330 | 4/1987 | Nelson et al. | 604/192 |
| 4,671,408 | 6/1987 | Raines et al. | 220/339 |
| 4,703,853 | 11/1987 | Byrns | 220/339 |

FOREIGN PATENT DOCUMENTS

| | | | |
|---|---|---|---|
| 713406 | 7/1965 | Canada . | |
| 2008963 | 9/1971 | Fed. Rep. of Germany . | |
| 2456495 | 1/1981 | France | 220/339 |
| 2597437 | 4/1986 | France | 206/349 |
| 0475267 | 10/1952 | Italy | 206/349 |

Primary Examiner—Paul T. Sewell
Assistant Examiner—David Jenny
Attorney, Agent, or Firm—Malloy & Malloy

[57] ABSTRACT

A package assembly designed to removably contain an elongated product wherein the product may particularly be a medical product such as a catheter or like instrument incorporating a sharp point end. The package is structured to provide secure storage of the medical product in a sterile environment prior to opening, clear exposure to a portion of the product for grasping and removal thereof and reinsertion of the product and enclosing thereof, so as to ensure safety in the disposal of the product by effectively enclosing the portion thereof incorporating a pointed needle end thereby avoiding inadvertent harm during or after the packaged product has been disposed.

10 Claims, 2 Drawing Sheets

PACKAGE ASSEMBLY

BACKGROUND OF THE INVENTION

1. Field of the Invention

The present invention relates to a package assembly designed to securely and safely enclose the product during storage and delivery to the point of use and also which may serve as a disposable container for the product wherein such product may have certain inadvertent dangers associated therewith such as a catheter type structure incorporating a sharp ended or pointed needle. The package assembly may further be characterized by almost total enclosure of a first portion of the product during storage, prior to use and after use for disposal as well as enclosure of a second portion of the product prior to and after use, but selective exposure of the second product portion to provide access thereto so as to efficiently accomplish removal of the product from the container prior to use and insertion therein after use and immediately prior to disposable.

2. Description of the Prior Art

Versatility and adaptability of the packing industry is notorious and well accepted. Such is evidenced by certain prior art packaging structures which are specifically designed and adapted to meet and overcome problems associated with the packaging of specialty products. While it is recognized that many products can be packaged either in bulk or in rather conventional multi-sided containers, it is also recognized that there are many products having specialized requirements for storage, display, etc. This is true particularly but not exclusively when dealing with medical products. Such products frequently have to be stored for a relatively long period of time until the individual product or products packaged together are ready for use. During such storage, and immediately prior to or subsequent to the packaging of these products, a sterilization process must be undergone so that the product may be stored in a "sterile environment" up to the point of use wherein the packages are then opened to provide exposure to the product and removal from the package.

Yet other problems are specifically directed to medical products having a needle or catheter type structure wherein a certain protective measure has to be considered in the initial packaging, storage and disposal of such products. This is of course due to the fact that such products incorporate a needle or pointed end structure which is specifically designed to penetrate the skin and possible blood vessel portions of the body during use. It is important therefore to prevent or at least significantly reduce the tendency of damage being done to more susceptible positions of the product, such as a sharpened point or tip. Such a product must be securely mounted within the package in order to avoid such damage. Also, in order to prevent inadvertent damage to personnel which handle the packaging both prior and subsequent to the use thereof, certain protective measures have to be incorporated in the packaging structure itself in order that the potentially danger portions thereof such as the pointed end of the needle be enclosed or otherwise shielded. Therefore, the aforementioned shielding or enclosing of dangerous portions of a given product must be considered not only during the storage and display of a product, but after use thereof during disposal since many products present a safety hazard when disposed of without first being inserted in some type of housing, closure, shielding structure, etc.

Regarding specific types of existing packaging, it is known to form a package by joining a first molded part to a second molded part, but such fabrication procedures have obvious disadvantages. To the contrary, it would be preferable to have a package structure of substantially one piece construction capable of safely and securely mounting a product therein while at the same time facilitating removal of the product for use and reinsertion of the product after use, for disposal.

There is a need in the packaging industry for a specialized package capable of having structural features allowing it to be sufficiently versatile for the safe and secure containment of a number of products, not necessarily limited to the medical field, but which clearly offers protection to potentially dangerous portions of the product such as pointed ends. At the same time such a preferred package should allow the product to be sterilized and maintained in a sterile environment prior to opening the package at the point of use. Further, a preferred packaging for this type of product should be capable of housing or maintaining the product or at least potentially dangerous portions thereof in an enclosed, shielded location to prevent inadvertent harm or damage to those unknowingly handling disposal of these types of products.

SUMMARY OF THE INVENTION

This invention relates to a packaging assembly specifically structured to removably contain a product in a manner such that potentially dangerous portions of the product such as sharp or pointed ends, etc., are securely mounted and protected therein and adequately shielded. The product may be maintained in a sterile environment for relatively long storage periods yet easily openable, at least in part, to provide ready access to a portion of the product and removal of the product from the package for use. In addition, the structure of the package is such as to be used as a disposable container for the product to the extent that the product may be reinserted within the package, or at least portions thereof may be reclosed or resealed. Any potentially dangerous portions of the product are protectively secured during storage prior to use and shielded after use and during disposal, thereby preventing inadvertent injury to unwary handlers of trash or other disposed of supplies or like products. While the present invention is primarily described for use in the packaging of a medical product such as a catheter structure, intravenous needle structure or the like it is not limited to such specialized products. To the contrary, the basic structural features of the subject package assembly as set forth in greater detail hereinafter, could be used for the packaging of a wide variety of articles particularly where protection of the product and its maintenance in a sterile environment is necessary or desirable and/or where the package, after use of the product can also be used as a disposal container in which the product is placed and effectively enclosed.

Generally, the package assembly of the present invention comprises a base having a hollow interior defining a storage chamber which preferably is in the form of a closed cylinder such that a first portion of the product for example the needle portion of the catheter structure, is maintained in an enclosed and protected position during storage and immediately prior to use. The package assembly further comprises a closure means including at least one but preferably two closure segments pivotally or otherwise movably secured adjacent the proximal open end of the base. The closure segments may be of equivalent or corresponding dimension and configuration and be mounted on opposite sides of the base. The movable or pivotal connection of the closure segments allow their selective positioning between an opened and closed position relative to a second portion of the product protruding outwardly from the base and oppositely disposed relative to the first portion of the product maintained within the aforementioned storage container of the base.

A closed position of the closure segments is defined by there mating and preferably sealing engagement with one another as they extend along the length of the second portion of the product and, due to there corresponding configuration, in surrounding and enclosing relation thereto. A latch means or like closing facility may be secured to the closure means or between the closure segments so as to maintain the closure segments in the closed position.

Operative manipulation of the latch means and a physical displacement of the closure segments away from one another positions the closure segments in there opened position. Such opened position is defined by a substantially outward extension of the closure segments relative to the base and to the product itself. This opened position allows clear exposure of the second portion of the product to facilitate ease and removal thereof from the package assembly.

The closure segments of the closure means are also cooperatively structured with one another and with the base to allow a reinsertion of the subject product, after use, back into the package assembly. In such instance, the subject package assembly may therefore be used as a disposal container wherein the needle and particularly the sharpened point or tip thereof is fully enclosed and therefore protected from inadvertent puncture or damage to handlers of the packaged product after use such as when removing trash or supplies from a disposal area. Particularly, the base is disposed at all times in surrounding relation to the enclosed storage container whereby access thereto is only provided through the opened proximal end thereof. The proximal end is specifically dimensioned, disposed and configured to allow removal of the first portion of the product therefrom as well as reinsertion therein for purposes of disposal. The closure segments are structured when used with or without the latch means to be opened, for removal of the product from the package assembly and for reclosing after the product has been used and reinserted in the package for disposal. Accordingly, a protective housing of the product and in particular potentially dangerous or fragile portions thereof, is provided during storage of the product prior to and after use of the product.

Another feature of the present invention is the provision of a protective shroud or covering disposed in surrounding relation to at least the closure segment, when in there closed position. Such shroud means may take the form of a wax or like material coating or alternately a heat shrinkable plastic film or wrap material. While providing additional assurances of the product will be maintained in a sterile state such a shroud means also assures a user of the product that tampering or previous, unauthorized access has not been obtained to the product. Any such tampering would of course be evidenced by a breaking or rupturing of the shroud means in any of the many forms that it may take.

The invention accordingly comprises the features of construction, a combination of elements and an arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
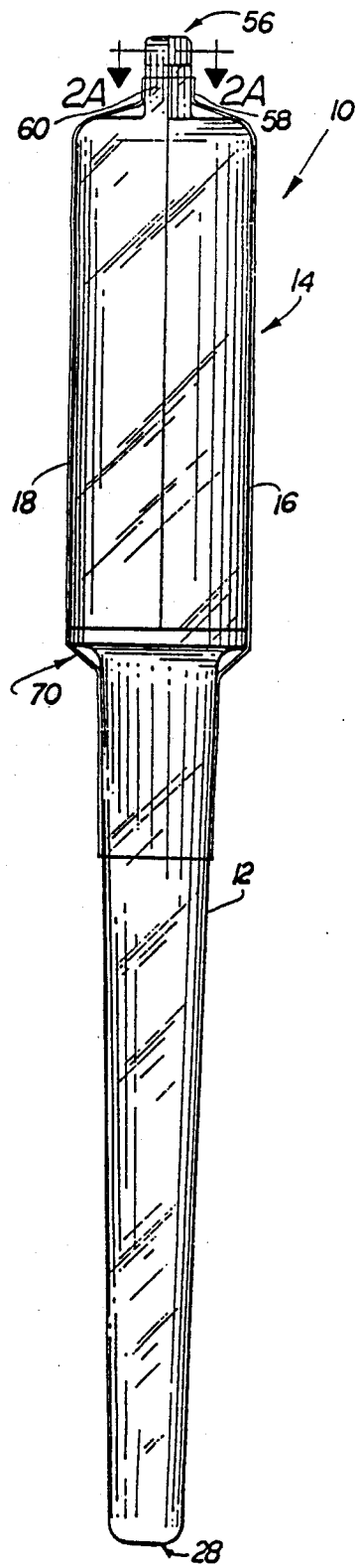
FIG. 1 is a front elevation of the package assembly of the present invention in its closed configuration.

As shown in FIGS. 1 through 5 the present invention is directed towards a packaging assembly generally indicated as 10 having a base 12 and a closure means generally indicated as 14. The closure means 14 comprises two closure segments 16 and 18 pivotally secured to substantially opposite sides of the base 12 substantially adjacent an opened proximal end thereof as at 20. In a preferred embodiment base 12 has a substantially closed cylindrical configuration extending along the length of a first portion 22 of an internally contained product generally indicated as 24. The base 12 is correspondingly elongated relative to the first portion 22 of the product and has a longitudinal dimension at least minimally greater than the first portion 22 so as to extend beyond and cover the end 26 of the first portion 22 by the distal end generally indicated as 28 of the base 12. As will be explained in greater detail hereinafter the distal end 28 may incorporate a filter type vent means generally indicated as 30 or be totally closed (see FIG. 6) as at 28'. Accordingly, it should be apparent that the base 12 of the package assembly 10 is such as to effectively close, securely mount and adequately protect the first portion 22 of the product 24 from an external damage due to dropping, etc. However, the base 12 is configured in surrounding and enclosing relation particularly to the tip or end 26 which may possibly be considered a potentially dangerous part of the product 24 in that it is sharpened and represents the pointed or sharpened part of a needle or catheter structure. It is to be emphasized herein that the package assembly 10 of the present invention is not limited merely for the packaging and protection of a medical product or a catheter type structure 24, but to the contrary a variety of articles of varying shapes and structural configuration as will be more apparent after a more detailed discussion of the structural features of which the package assembly 10 is comprised.

A support means is located in part generally as at 32 and comprises a restricted structure or portion 34 engaging what may be considered the base of the stem of the product 24 as at 25. In addition, the support means 32 includes a continuous annularly configured upstanding skirt 36 surrounding generally the stem 25 of product 24 and serving to embrace, engage, support and maintain the first portion 22 as well as the pointed tip 26 of the product 24 in a somewhat suspended relation within the interior of the base 12 which may be defined as a storage chamber 15.

Figure 2:
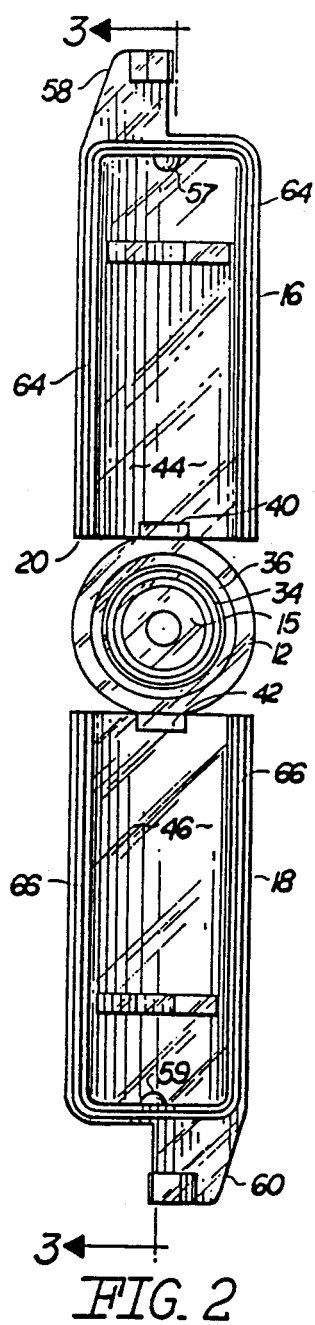
FIG. 2 is a top elevation of the package assembly of the present invention in its opened configuration.

As set forth above, the package assembly 10 also includes the closure means 14 comprising closure segments 16 and 18. These closure segments are pivotally connected by hinge or pivot structures 40 and 42 disposed in interconnecting relation on substantially opposite sides of the proximal open end 20 of base 12 as best shown in FIG. 2. Such pivotal interconnection 40 and 42 allows selective positioning between an open position (see FIGS. 2 and 3) and a closed position as shown in FIG. 1 and represented in phantom lines in FIG. 3. Each closure segment 16 and 18 is preferably configured to have an at least partially hollow interior portion and thereby form a container segment 44 and 46 on the interior thereof respectively. Further, the dimension and configuration of the closure segments 16 and 18 are substantially equivalent and the interior of the chambers 44 and 46 are such as to collectively surround a second portion 23 of the product 24 when the segments 16 and 18 are in there closed position. For purposes of specificity the second portion 23 of the product 24 is defined as that portion of the product which does not extend into the storage chamber 15 but to the contrary extends outwardly therefrom so as to be exposed to accomplish ready removal of the product 24 from the package assembly 10 when the closure segments 16 and 18 are positioned or maintained in there open position. Further, the interior surface of each closure segment 16 and 18 is positioned so as to engage, at least in part, the exterior surface of the annular skirt 36 thereby enhancing any sealing closure of segments 16 and 18 when in their closed position. The respective interior surfaces 44' and 46' are further dimensioned so as to be maintained in a somewhat spaced apart relation to the exterior surface of the second portion 23 of the product. However, stability of the product is maintained as it is enclosed within the package assembly 10 through the provision of additional structure of support means comprising two support elements 50 and 52.

Figure 4:
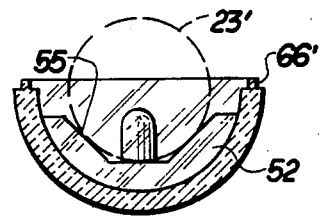
FIGS. 4 and 5 are sectional views respectively along lines 4—4 and 5—5 of FIG. 3 showing structural details of the closure segments of the subject package assembly and wherein the product placement relative to the closure segments is represented in phantom lines.
Figure 5:
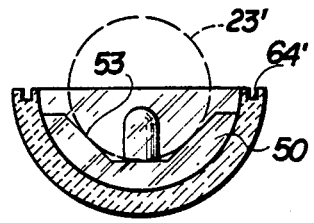

Each of the support elements 50 and 52 (see FIGS. 3, 4 and 5) are preferably integrally formed and extend outwardly from the respective inner surfaces 44' and 46' of the segments 16 and 18 respectively. The degree of outer extension is such that the outer ends 53 and 55 of the respective support elements 50 and 52 are configured to at least partially or substantially correspond to the outer surface 23' of the second portion 23 of the product 24 as best shown in FIGS. 4 and 5. The engagement of the support members 52 and 53 on opposite sides of the second portion 23 of the product 24 ensures a stable fit of the product 24 within the package assembly when the closure segments 16 and 18 are in there closed position. A third and fourth support structures 57 and 59 are similarly integrally formed on the respective inner surfaces 44' and 46' of the respective closure segments 16 and 18 and disposed to engage an outer most extremity 23" of the second portion 23 of product 24 as represented in phantom lines in FIG. 3.

Figure 2A:
FIG. 2A is a sectional view in partial cutaway along line 2A—2A of FIG. 1.

Further structural features of the present invention is the provision of a latch means generally indicated as 56 and structured to include a latch segment 58 and 60 respectively formed on each of the closure segments 16 and 18 at the outer end thereof. The actual latch structure is represented in detail in FIG. 2A and shows cooperatively configured mating surfaces 62 and 63 disposed in mating engagement with one another. The mating surfaces 62 and 63 are integrally formed on upstanding latch segments 58 and 60 as shown.

Yet another feature of the present invention is the mating engagement of the closure segments 16 and 18 about correspondingly positioned continuous peripheries. Each continuous periphery of each closure segments 16 and 18 is represented by a peripheral edge 64 and 66 which as more specifically shown in FIGS. 4 and 5 comprise respectively an elongated continuously formed groove or channel 64' and an outwardly projecting continuously formed flange 66'. The groove 64' and the tongue 66' defining the respective peripheral edges of the closure means 16 and 18 are cooperatively disposed, dimensioned and configured such that the tongue 66' mates within and provides a closing engagement with the groove 64'. Such mating engagement also defines what may be referred to as a "tortuous" path which is resistant to the inflow or passage of bacteria from the exterior of the package through this tongue and groove engagement.

Figure 3:
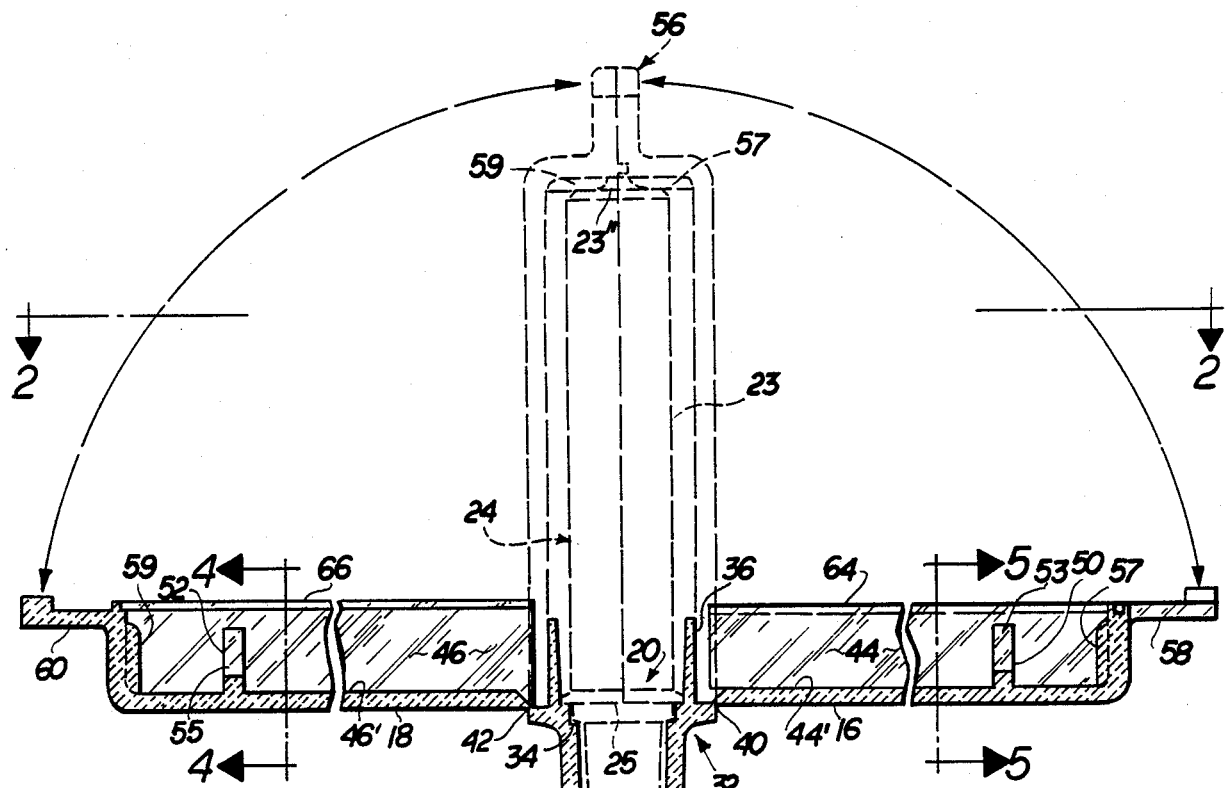
FIG. 3 is a longitudinal sectional view along line 3—3 of FIG. 2 showing a product contained therein represented in phantom lines and closure segments of the package assembly shown in there closed position in phantom lines.
Figure 6:
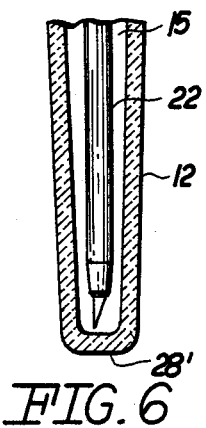
FIG. 6 is a sectional view in partial cutaway showing another embodiment of a portion of the base of the subject packages assembly.

With regard to the different embodiments shown best in FIGS. 3 and 6, the distal end 28 of the base 12 may be formed with a filter means generally indicated as 30. The filter means 30 includes a filter disk 31 formed of a material which is resistant to the passage of bacteria therethrough but which allows air or gas to pass between the interior and exterior chamber of the storage 15 or remainder of the package assembly 10. Such venting of gas through disk 31 may occur when the package assembly 10 and the product 24 maintained inside is in fact sterilized while in the package other than by means of radiation. The other embodiment shown in FIG. 6 is the closed distal end 28' having no such vent of filter means.

Yet another feature of the present invention is the provision of a shroud or exterior coating or film disposed over at least a portion of the length of the package assembly 10 and particularly over a majority of the closure means 14. This shroud means generally indicated as 70 may take the form of a heat shrinkable plastic film or wrap material or alternately may take the form of a wax or like coating initially applied in a somewhat melted form which rapidly solidifies after being exposed to the atmosphere or otherwise cooled. In either event, such shroud means 70 provides additional assurances that the product 24 will be maintained in a sterile state on the interior of the package assembly 10 and resist the inflow into the interior of package assembly 10 of bacteria. The shroud means 70 performs an additional function of serving as a tampered proof addition to prevent or at least indicate unauthorized entry into the package.

Now that the invention has been described, what is claimed is:

1. A package assembly designed to removably contain a single, substantially elongated product, said package assembly comprising:
   (a) an elongated base having a closed cylindrical configuration extending along its length and having a hollow interior defining a storage chamber therein and including an open proximal end and a substantially closed distal end and configured to have a greater length than a first portion of the product contained within said storage chamber,
   (b) closure means secured to said base for enclosing a second portion of the product which extends outwardly of said storage chamber through said open proximal end, said closure means comprising two closure segments each pivotally connected to said base adjacent said open proximal end and on substantially opposite sides thereof and selectively disposable between an open and a closed position,
   (c) said open position defined by each of said closure segments connected to and extending outwardly from said base and the product therein, said closed position defined by said closure segments collectively disposed in surrounding relation to the second portion of the product,
   (d) said closure means structured to expose the second portion of the product, for removal of the product from said storage chamber, when said closure segments are in said open position and further enclose the second portion of the product between and within said closure segments when in said closed position,
   (e) a support means formed in part on each of said closure segments and extending outwardly therefrom for engagement of the second portion of the product when said closure segments are in said closed position, and
   (f) a substantially annularly configured skirt formed on said base and extending axially outward from said open proximal end and disposed in engagable relation with the product and with interior surface portions of each closure segment when said closure segments are in said closed position.

2. A package assembly as in claim 1 wherein said closure segments are integrally secured to said base and said closure means and said base are formed of a lightweight, plastic disposable material.

3. A package assembly as in claim 1 wherein each of said closure elements includes a supplementary support structure formed on the interior surface thereof and each disposed to engage an outer end of the second portion of the product when said closure segments are in said closed position whereby suspension and retention of the product within said package assembly is facilitated.

4. An assembly as in claim 1 wherein each of said closure segments defining a continuous peripheral edge and one of said peripheral edges on said continuous periphery comprises an outwardly extending tongue extending continuously along its length and the other of said peripheral edges comprises a groove extending along the length thereof and dimensioned to receive said tongue.

5. An assembly as in claim 1 further comprising a filter means disposed adjacent said distal end and structured and dimensioned for the restriction of the in flow of bacteria into said storage chamber when said closure means is in said closed position.

6. An assembly as in claim 1 wherein the peripheries of both or said closure segments are defined by separate integrally formed peripheral edges, one of said peripheral edges comprising an outstanding flange extending continuously along the length thereof and the other of said peripheral edges comprising a recessed groove extending continuously along the length thereof, said groove being dimensioned and configured to receive said flange therein when said closure segments are in said closed position.

7. An assembly as in claim 1 further comprising filter means disposed adjacent said distal end and disposed in communicating relation with an exterior of said storage chamber and structured for restriction of the end flow of bacteria therethrough into said storage chamber.

8. An assembly as in claim 1 wherein said support means further comprising a restrictive structure mounted on said base and dimensioned for engagable supporting relation to the first portion of the product for disposition thereof into said storage chamber.

9. A package assembly as in claim 1 further comprising shroud means formed in surrounding, enclosing relation to said closure means for restricting and indicating unauthorized entry to the product.

10. An assembly as in claim 1 further comprising latch means mounted at least in part on said closure means as structure for removable securement of said closure segments to one another.

* * * * *